US005548994A

United States Patent [19]
Selby et al.

[11] Patent Number: 5,548,994
[45] Date of Patent: Aug. 27, 1996

[54] STATOR CONNECTOR

[75] Inventors: Theodore W. Selby; Kevin J. Wolfe, both of Midland; William A. Atkins, Bay City, all of Mich.

[73] Assignee: Tannas Co., Midland, Mich.

[21] Appl. No.: 486,881

[22] Filed: Jun. 7, 1995

Related U.S. Application Data

[63] Continuation-in-part of Ser. No. 308,918, Sep. 20, 1994, Pat. No. 5,513,517.

[51] Int. Cl.⁶ .................................................. G01N 11/14
[52] U.S. Cl. ........................................ 73/54.28; 73/54.35
[58] Field of Search ............................... 73/54.28, 54.29, 73/54.31, 54.32, 54.33, 54.34, 54.35

[56] References Cited

U.S. PATENT DOCUMENTS

| | | | |
|---|---|---|---|
| 2,519,378 | 8/1950 | Kilpatrick | 73/59 |
| 2,573,505 | 10/1951 | Steffens. | |
| 2,679,750 | 6/1954 | Brookfield. | |
| 2,957,339 | 10/1960 | Penny et al.. | |
| 3,572,086 | 3/1969 | Johnston | 73/59 |
| 3,611,789 | 10/1971 | Lopas | 73/59 |
| 3,935,726 | 2/1976 | Heinz | 73/60 |
| 4,062,225 | 12/1977 | Murphy et al. | 73/60 |
| 4,214,475 | 7/1980 | Carter et al. | 73/59 |
| 4,299,118 | 11/1981 | Gau et al. | 73/59 |
| 4,448,061 | 5/1984 | Brookfiled | 73/59 |
| 4,648,263 | 3/1987 | Deysarkar et al. | 73/59 |

OTHER PUBLICATIONS

ASTM D 5153-90.
VanMeter, U.S. Ser. No. 08/336379 filed Nov. 8, 1994, specification as filed.
VanMeter et al., U.S. Ser. No. 08/308918 filed Sep. 20, 1994, specification as filed.
VanMeter et al., U.S. Ser. No. 29/030792 filed Nov. 8, 1994, specification as filed.

*Primary Examiner*—Hezron E. Williams
*Assistant Examiner*—Jay L. Politzer
*Attorney, Agent, or Firm*—Christopher John Rudy

[57] ABSTRACT

A stator for a sensitive rotating viscometer is directly connected to the viscometer module housing or the viscometer module lower housing (rotor housing) particularly on lower portions or about the side of the same.

16 Claims, 6 Drawing Sheets

STATOR CONNECTOR

CROSS-REFERENCE

This is a continuation-in-part of application Ser. No. 08/308918 filed Sep. 20, 1994 U.S. Pat. No. 5,513,517 (May 7, 1996).

FIELD

The present invention concerns a sensitive rotating viscometer with a stator connection therefor and therein, and the stator itself, useful in measuring fluid viscosity.

BACKGROUND

The configuration of most rotational viscometers requires a rotating element called the rotor and a stationary element called the stator, which contains the fluid to be tested for properties such as viscosity, and in which most typically the rotor rotates in contact with the fluid so as to determine drag caused by the fluid. This drag can then be related to the viscosity of the fluid.

Rotational viscometers such as the Brookfield viscometer are well-known instruments for measuring viscosities of liquids. Usually, the rotor, which is driven by a motor in the Brookfield head or module, is immersed in a large container of liquid in which the walls of the container are at some considerable distance from the rotor and thus have little influence on the measurement of the viscous value. This container is the stator. In some applications such as in the well-known Scanning Brookfield Technique, discovered and developed by Mr. Theodore W. Selby and licensed to the Tannas Co., Midland, Mich., and used in ASTM D 5133, incorporated herein by reference as its 1990 version, the rotor must be relatively close to the stator wall to gain the necessary sensitivity. In such a case, the rotor must be centered carefully.

Typically, the stator is fixed to the Brookfield module by means of a stator collar. See e.g., Deysarkar et al., U.S. Pat. No. 4,648,263 (Mar. 10, 1987).

In practice, problems are encountered with the commercially available support and centering attachment as of Deysarkar et al., which is known commercially as the Pennzoil/Tannas rotor/stator centering adapter, Tannas Model Number SBV-P. In particular, and in reference to the foregoing patent, an O-ring, present in the SBV-P adapter in a slot cut in interior surface 54 of cylindrical member 70, can swell as from contact with solvents or oil to the point where sometimes, upon the contraction of the constraining cylindrical member 70, a glass stator 28 may be difficult to remove or actually break in removal. The O-ring also may become worn or oily, and, if a loose fit between cylinder member 70 and stator 28 is engendered, slippage and rotation of the stator occurs during testing, which destroys the value of the test. Furthermore, the O-ring can be difficult to install and remove for replacement. Another effect of low-temperature contraction of cylindrical member 70 is that when bath 44 controls the test liquid temperature at minus forty degrees C., or below, separation of parts of device 40, to include removal of a glass stator 28, filled with tested liquid, from the lower end 52 of the device, becomes very difficult because of the aforementioned contraction of the engineering thermoplastic employed to make the adapter.

A further problem in low-temperature viscometry is the need to introduce dry air or gas above the liquid being cooled so that the surface of the oil does not gather moisture and form ice.

Accordingly, research has been directed at solving such problems at the Tannas Co. Note in this connection the following U.S. patent applications: Van Meter et al., Ser. No. 08/308,918, filed on Sep. 20, 1994, U.S. Pat. No. 5,513,517 (May 7, 1996), entitled ROTOR-STATOR ADAPTER FOR SENSITIVE ROTATING VISCOMETERS; Van Meter, Ser. No. 08/336,379, filed on Nov. 8, 1994, U.S. Pat. No. 5,517,850 (May 21, 1996) entitled ROTOR-STATOR ADAPTERS WITH INTERNALLY THREADED STATOR COLLAR & EXTERNALLY THREADED NUT FOR SENSITIVE ROTATING VISCOMETERS. See also, Van Meter et al., design Ser. No. 29/030,792, filed on Nov. 8, 1994, entitled COLLAR HOUSING FOR A ROTOR-STATOR ADAPTOR FOR SENSITIVE ROTATING VISCOMETERS, which issued on Nov. 21, 1995 as Des. 364,351. Each of these inventions involves a stator collar, improvements over the support and centering device of Deysarkar et al., and the commercial model SBV-P.

However, manufacture and commercialization of such adapters or stator collars is, in general, not without noteworthy expense. Moreover, the requirement of an adapter or stator collar can present an additional investment in operator training, and equipment upkeep.

What is needed is an arrangement or article which overcomes such problems or hurdles, while providing for precise centering of the rotor spindle in the stator of a sensitive rotating viscometer. It should be readily manufacturable and commercializable—and be efficient to operate, especially by inexperienced operators.

OBJECTS

It is an object of the present invention to overcome or ameliorate problems in the art such as aforesaid.

It is an object hereof to avoid an adapter such as of the patent to Deysarkar et al.

It is an object hereof to avoid problems or drawbacks associated with the presence of an adapter or stator collar in a sensitive rotating viscometer as aforesaid.

It is an object hereof to provide for precise centering of the rotor spindle in the stator of such a viscometer.

It is an object hereof to provide for simple introduction of dry air or gas to protect the liquid surface from moist air.

It is an object hereof to provide a readily manufacturable arrangement.

It is an object hereof to provide a readily commercializable arrangement.

It is an object hereof to provide an efficiently operable arrangement, especially by even inexperienced operators.

Further objects hereof are extant, to include as may be ascertained from the present specification.

SUMMARY

The present invention provides, in one aspect, in a sensitive rotating viscometer having a module in which resides a motor for rotating a rotor attachable to a shaft of the motor, the rotor having a longitudinal axis and being rotatable about its longitudinal axis, being typically pivotally suspended from the shaft about to a lower end of the viscometer module, and generally cooperating with a stator and a predetermined quantity of test fluid in the stator, and being suspended within the stator in which the test fluid can be contained for contact with the rotor, so that, when the rotor rotates therein, drag is created on the rotating rotor related to viscosity of the test fluid, the improvement which comprises a fixable stator connected to the module of the viscometer through a proximate stator connector. Another aspect hereof can include the fixable stator itself.

The invention is useful in assisting the measurement of viscosity.

Significantly, the invention achieves all or at least some of its objects and solves or ameliorates problems in the art as aforesaid. More particularly, the invention avoids the aforementioned adapters or O-ring-containing stator collars, and hence, problems associated with the same or the like. It is readily manufacturable and commercializable; it provides for precise centering of the rotor within the stator, and it is easily operable, especially by even inexperienced operators.

Numerous further advantages attend the invention.

DRAWINGS

The drawings form part of the specification hereof. In the drawings, in which like numerals refer to like features, the following is briefly noted.

ILLUSTRATIVE DETAIL

The patents, pending patent specifications, and other publications mentioned anywhere in the present specification are incorporated herein by reference.

The invention can be further understood by reference to the present detail and drawings, which are to be construed as illustrative and not necessarily limiting in nature.

Figure 1:
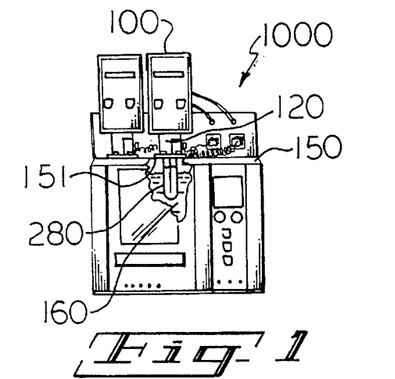
FIG. 1 is a front, partial cut-away view of a sensitive rotating viscometer, improved with stator connectors of the invention.
Figure 2:
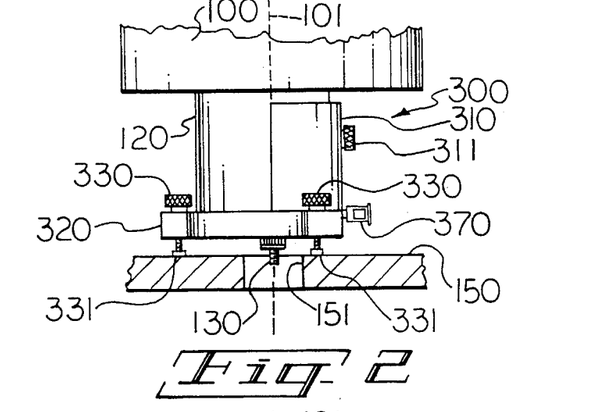
FIG. 2 is a side view of a stator connector as present in FIG. 1.
Figure 3:
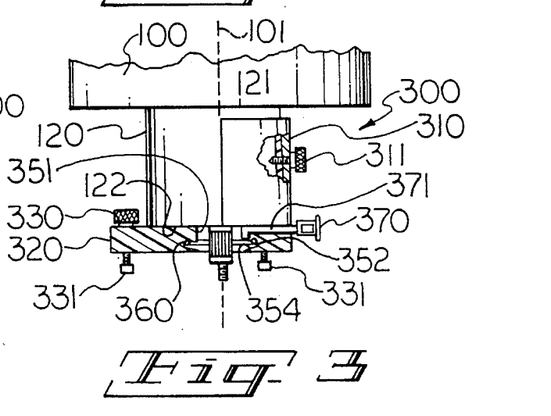
FIG. 3 is a side, partial cut-away view of the stator connector of FIG. 2.
Figure 4:
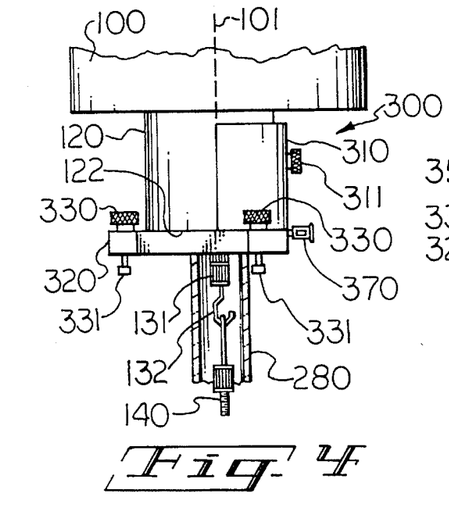
FIG. 4 is a side view of the stator connector of FIG. 2, with a rotor spindle and stator attached.

In reference to the drawing figures, within FIGS. 1 et seq., sensitive rotating viscometer 1000 has viscometer module 100 which houses a motor (not illustrated) and so forth. Along axis of rotation 101, in general, from lower end 120 of the module 100 protrudes rotatable motor shaft 130. An adapter 131, mounting on the shaft 130, can have pivot notch or hook 132 for pivotally mounting a rotor spindle 140 which rotates in test liquid 99, for example, a gear oil, motor oil, automatic transmission fluid, or other oleaginous or hydrophilic liquid, contained in stator 280. The stator 280 contains the test liquid 99 and is attached for testing.

Stator connector 300 may attach directly to the viscometer lower end 120 (FIGS. 1–7) or be made integrally therewith (FIGS. 8–10 & 12). Modifications from combining features of attachment and integrally making of a stator connector with the viscometer module 100 can be made such as by integrally making a portion of the stator connector with the module and attaching the remaining portions of the stator connector to the module, and such are within the practice of the present invention.

In reference to FIGS. 1–5 and 6 & 7, the stator connector 300 has semi-cylindrical attachment member 310 to be attached to standard cylindrical viscometer lower end 120 of viscometer module 100 such as with the Model TAV-2 rotating viscometer module available from Tannas Co., Midland, Mich., although other shapes of the attachment member 310 are possible, which preferably conform to the shape of the lower end 120. Attachment may be by attaching screw 311, which is threaded to mate with tapped lower end attachment hole 121. Attached to or integral with the attachment member 310 is base plate 320, which is generally oriented horizontally and normal to the attachment member 310, and upon which rests a bottom surface 122 of the lower end 120 of the viscometer module 100. Leveling screw holes 321, generally three or four in number, and preferably four for greater stability, accommodate leveling screws 330. Bases 331 of the leveling screws 330 contact top surface 150 of viscometer 1000, which has a hole 151 therein to permit insertion of the shaft 130 and/or its attachments to include rotor spindle 140 as in stator 280 to be inserted into temperature control bath liquid 160 of the viscometer 1000 for testing. O-ring 340 or other flexible washer may be present to seal top of the stator 280. It is in base opening 350, having a primary hole 351, a larger, stator-accommodating recess 352 and perhaps an O-ring groove 353, that the washer 340 is placed. A stator lip-retaining ledge 354, which need not extend a great distance circumferentially and thus may be at a generally localized position, is retained at the boundary of the opening. The ledge 354 extends inside the lateral, or horizontally-extending, depth of the portion of the stator-accommodating recess 352 proximate thereto. Movable ledge 360 can clip lip 281 of a stator 280 such as by lever action and contact with the underside of the lip 281 while the underside of the opposing portion of the lip 281 is held by the stationary stator lip-retaining ledge 354. Preferably, the ledges 354 & 360 oppose one another at a position of one hundred eighty degrees or so. The movable ledge 360 can be of a resilient or spring-like material or be spring loaded. Inert gas blanket introduction connection 370, for example, a LUER-LOCK TYGON plastic tubing air adapter, can be present with inert gas blanket conduit 371 to provide for relatively slow introduction of an inert gas, for example, dry air or nitrogen, for a blanket over test liquid 99 in the stator 280. Exit of the inert gas as during testing is by leakage from the Brookfield viscometer module above the introduction site. In additional reference to FIGS. 6 & 7, downwardly extending, stationary ledge member 355 and downwardly extendible, movable ledge member 365, for example, movable by pivoting, can assist in providing lateral support to opposite sides of the stator 280.

Figures 5, 6, 7, 8, 9:
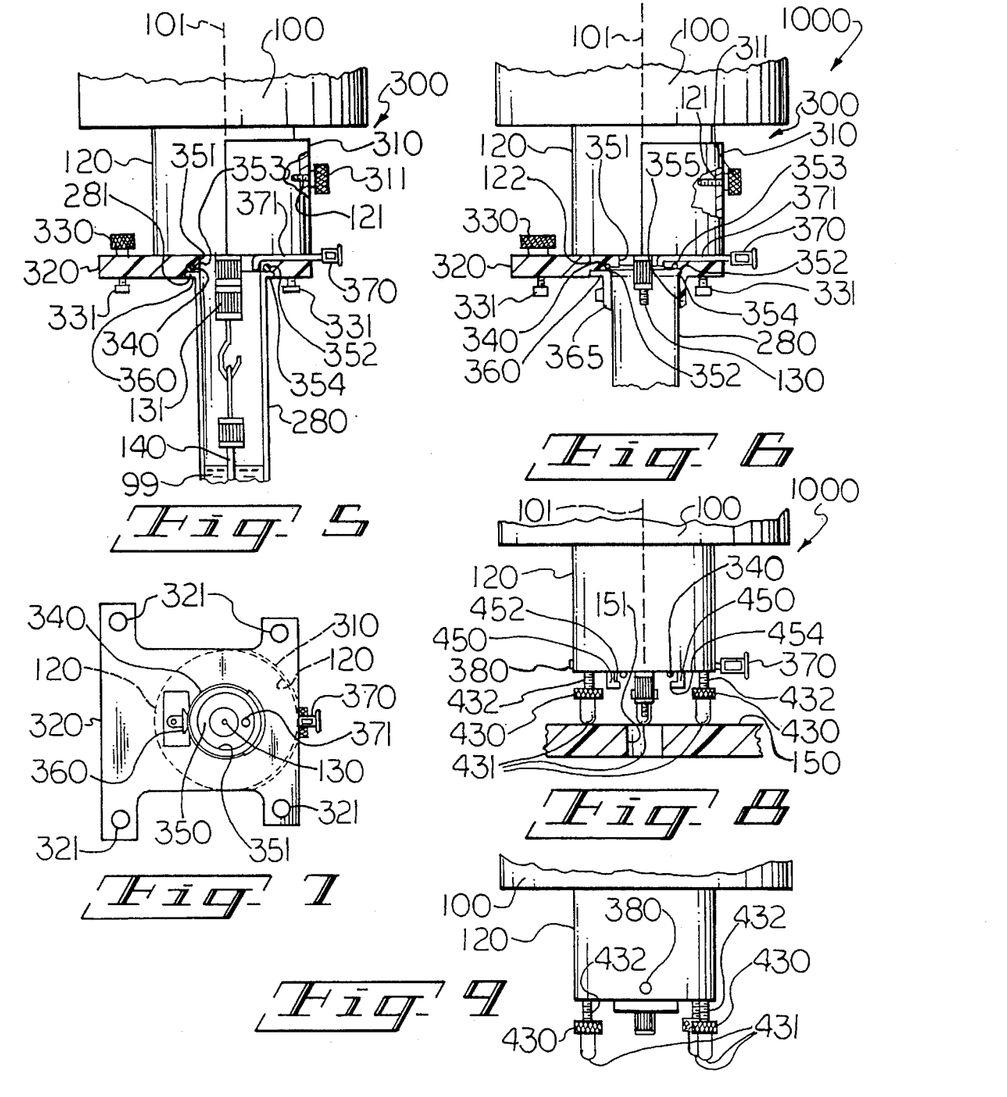
FIG. 5 is a side, partial cut-away view of the stator connector of FIG. 4.
FIG. 6 is a side, partial cut-away view of another embodiment of a stator connector of the invention, mounted on a sensitive rotating viscometer to improve the same.
FIG. 7 is a bottom view of the stator connector present in FIG. 6.
FIG. 8 is side view of another embodiment of a stator connector of the invention, mounted on a sensitive rotating viscometer to improve the same.
FIG. 9 is a front view of the stator connector of FIG. 8.
Figure 10:
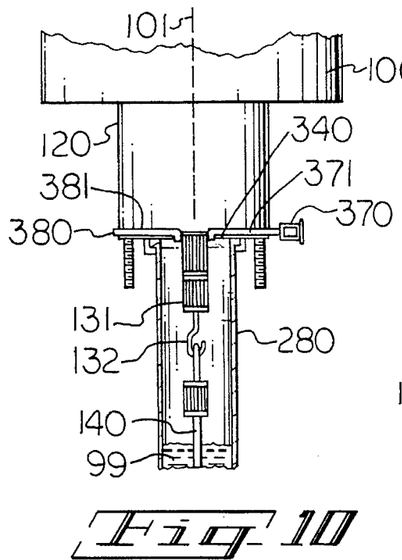
FIG. 10 is a side, partial cut-away view of the stator connector of FIG. 8, having a stator connected thereto.

In reference to FIGS. 8–10, and in supplement to the foregoing, attachment member 310 and base plate 320 as found in embodiments depicted in FIGS. 1–7 are not necessary. Rather, two L-shaped stator retention members 450 oppose each other at a distance suitable for insertion and retention of a stator 280 by lip 281. Each stator retention member 450 defines a stator-accommodating-retaining recess 452 and stator lip retaining, stationary ledge 454. This embodiment employs the bayonet-attachment principle. Accommodation may be made for a washer or O-ring 340, and so forth. Leveling nuts 430 have bases 431, which contact the top surface 150 of the viscometer 1000. The leveling nuts are screwed onto threaded studs 433, which are positioned in the lower end 120 of the viscometer module 100 of the viscometer 1000.

Figure 11:
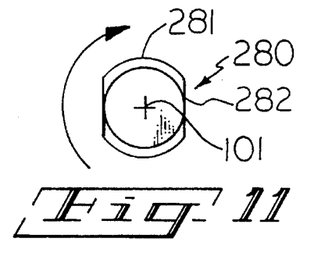
FIG. 11 is a top view of an improved stator of the invention, having a chordate lip, which can be employed in the stator connector of FIGS. 8–10.

In reference to FIG. 11, stator 280 has lip portion 281 and chordate lip 282. This stator is especially useful in an improved viscometer such as one having the two L-shaped stator retention members 450 as depicted in FIGS. 8–10. Therein, this stator is filled with test fluid and pulled up over rotor 140 attached to viscometer module 100 with its chordate lip portions passing up by and clearing the stationary ledges 454 until the top of the stator contacts any washer or O-ring 340. There the stator is rotated about ninety degrees, as generally depicted in FIG. 11, so that the lip portions 281 are moved into the stator-accommodating-retaining recesses 452 and held up by the stationary ledges 454.

Figure 12:
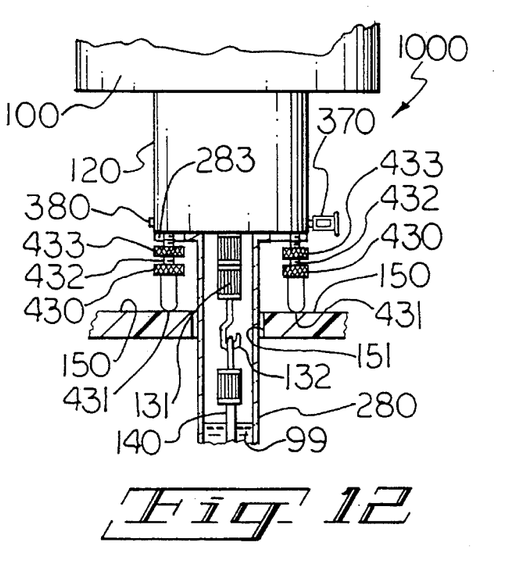
FIG. 12 is a side, partial cut-away view of another embodiment of a stator connector of the invention, to include another embodiment of an improved stator of the invention, mounted on a sensitive rotating viscometer to improve the same, with rotor spindle attached.
Figure 13:
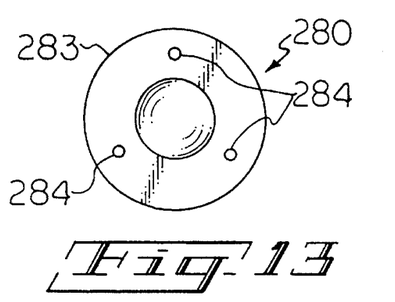
FIG. 13 is a top view of the improved stator present in FIG. 12.

In reference to FIGS. 12 & 13, stator 280 with wide lip 283 is retained in place through stator-retaining nuts 434. The threaded studs 433 go through stator lip retaining holes 284.

In additional reference to FIGS. 8–10, 12, 15 & 17, an inert gas exit orifice 380 provides for exit of inert gas through exit conduit 381 as during testing. This can provide for efficient flushing of the void space above the test liquid 99 in the stator 280 in provision of the inert gas blanket.

Figure 14:
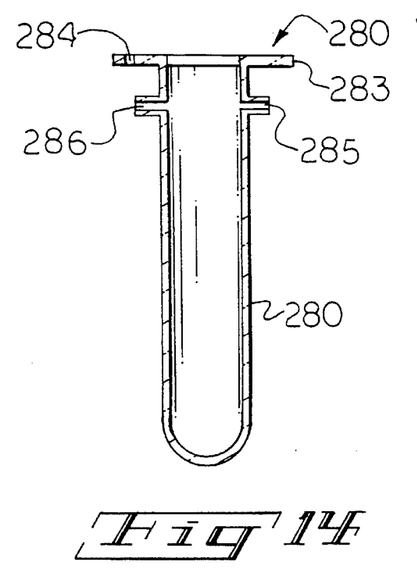
FIG. 14 is a side, cut-away view of another embodiment of an improved stator of the invention.

In reference to FIG. 14, stator 280 may have wide lip 283 and stator lip retaining holes 284 so as to be usable with a viscometer and stator connector as depicted in FIG. 12. This stator 280 has inert gas entry port 285 and inert gas exit port 286 for provision of an inert gas blanket, bypassing the need for inert gas connections and conduits in viscometer module or stator connector apparatus themselves.

Figure 15:
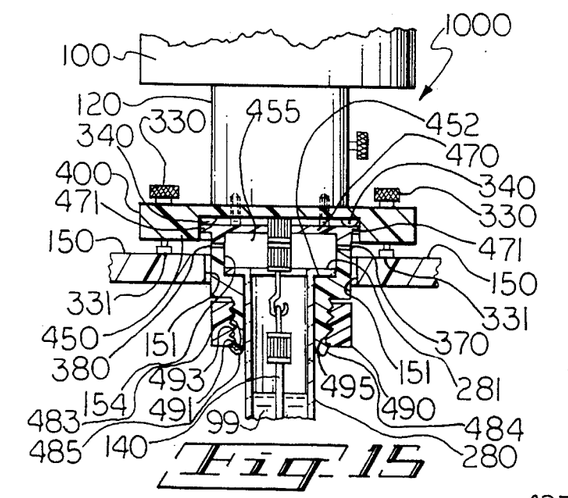
FIG. 15 is a side, cut-away view of another embodiment of a stator connector of the invention, mounted on a sensitive rotating viscometer, with a stator-holder in position ready for turning to secure it in place.
Figure 16:
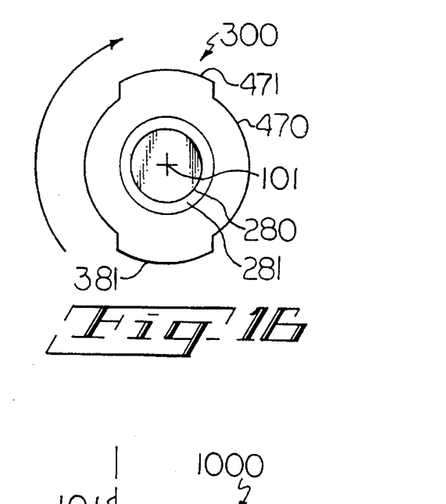
FIG. 16 is a top view of a stator-holder portion of the stator connector of FIG. 15.
Figure 17:
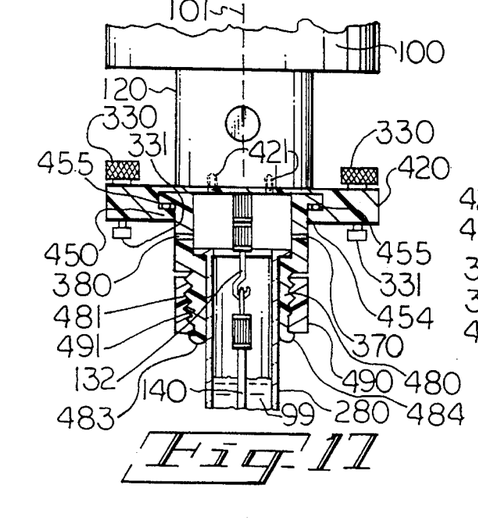
FIG. 17 is a front, cut-away view of the stator connector of FIG. 15, mounted on a sensitive rotating viscometer to improve the same, with its stator-holder secured in place.

In reference to FIGS. 15–17, the stator connector 300 has parts generally akin to the stator collar and nut pieces of the invention of Van Meter et al., Ser. No. 08/308,918. The present connector 300 includes collar 470 with lips or ears 471 proximate the top thereof. Inner cylindrical surface 154 of the stator collar is dimensioned to receive and encircle an upper end or lip 281 of the stator 280. The present connector 300 includes wall 480 which is externally threaded 481 in a lower portion thereof. The threaded wall is perforately slotted so as to provide by each slot an opening from the exterior to the interior of the wall, and preferably thus form fingers from a plurality of axially-directed slots. The wall has means to accept pressure and direct it inwardly such as, for example, may be provided by suitable tapered threads, or other surfaces, which may include protrusions, for example, a nut-retaining lip 483 on the stator collar 470, which may be squared, rounded or beveled at its lower, distal end 484, and capable of receiving the pressure and to have it directed inwardly. Such a pressure-receiving protrusion can be provided by a first, lower thread from among threads 481. As well, the present connector 300 has a nut 490, which is correspondingly, internally threaded 491 for attachment by threading about the threaded, slotted wall 480. The nut 490 has means to exert guiding pressure on the means to accept pressure of the wall 480 so as to cause it to be directed inwardly by tightening of the nut such as, for example, may be provided by suitably reverse-tapered threads, or other surfaces, which may include ramps or other suitable protrusions such as an internal reverse bevel 494. This generally causes snug contact between the lower interior surface 154 of the support member and the exterior cylindrical surface of a typical stator. In the collar 470, an external radial recess may be present for receiving a protrusion 485 of the nut 490. In the nut 490, an internal radial recess 493 may be present for receiving the protrusion 484 of the stator collar. The collar 470 is inserted into position between L-shaped stator retention members 450. Each stator retention member 450 defines a stator-accommodating-retaining recess 452 and stator lip retaining, stationary ledge 454. Ramps 455 apply upward pressure upon turning of collar 470 in the direction of the arrow in FIG. 16. This embodiment employs the bayonet-attachment principle. Accommodation may be made for a washer or O-ring 340, and so forth. Again, leveling screws 330, inserted into integral or attached base plate 420, have bases 331, which contact the top surface 150 of the viscometer 1000. The base plate 420 can be attached to lower end 120 of the viscometer module 100 by countersunk screws.

Figure 18:
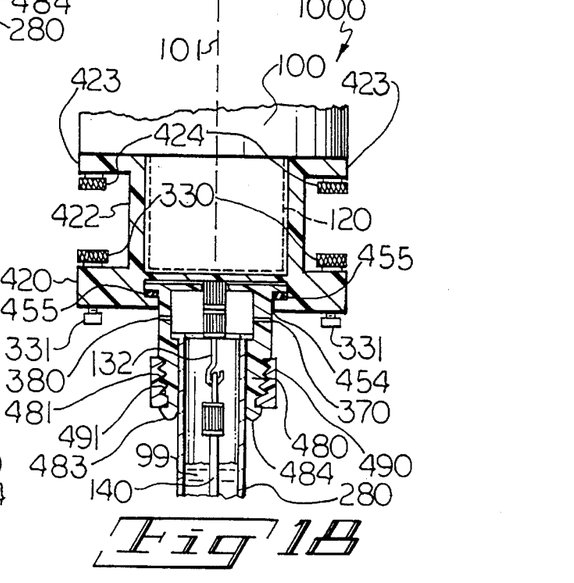
FIG. 18 is a side, cut-away view of another embodiment of a stator connector of the invention, assembled with a sensitive rotating viscometer to improve the same.

In reference to FIG. 18, the stator connector 300 has upright wall 422, which may house lower end 120 of the viscometer 100, projecting from the leveling base 420, which concludes in an upper base 423 which is attached to the viscometer module 100 directly by means of suitable fastener, for example, screws 424. Lower end 120 of the viscometer module 100 is bypassed and may be removed. Other features of this connector to secure the stator are present, for example, such as those present and described for the stator connector depicted in FIGS. 15–17.

Figure 19:
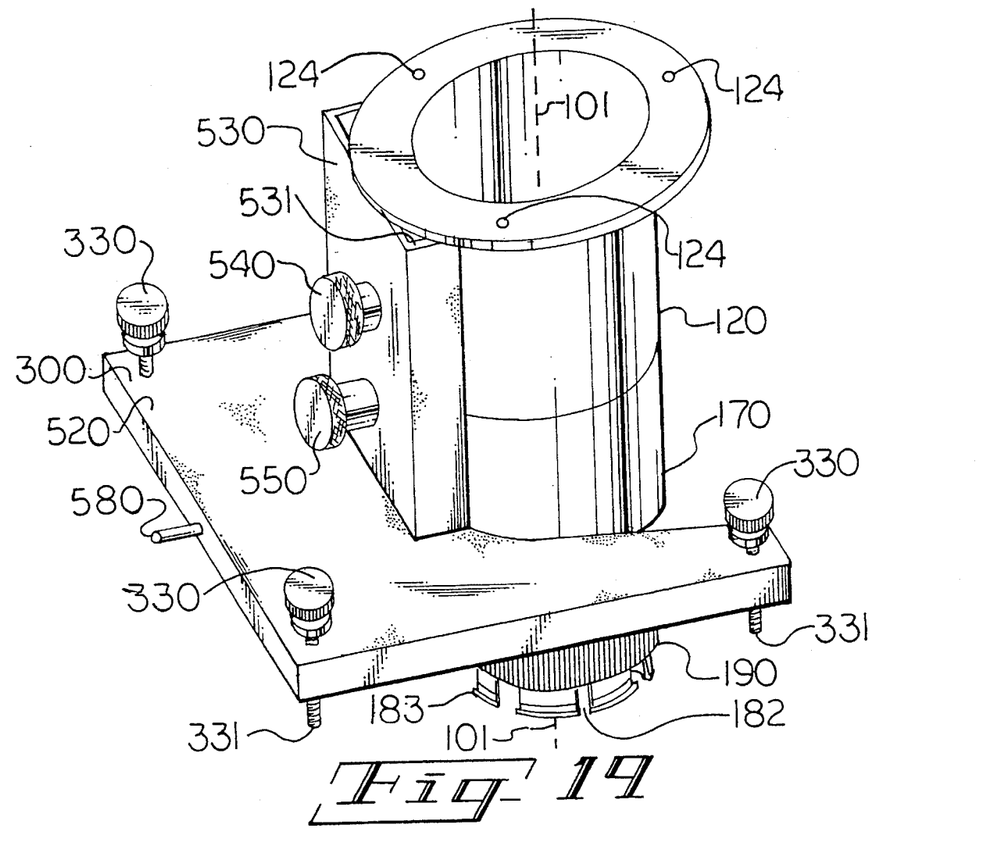
FIG. 19 is a top, side, rear perspective view of another embodiment of a stator connector of the invention.
Figures 20, 21, 22:
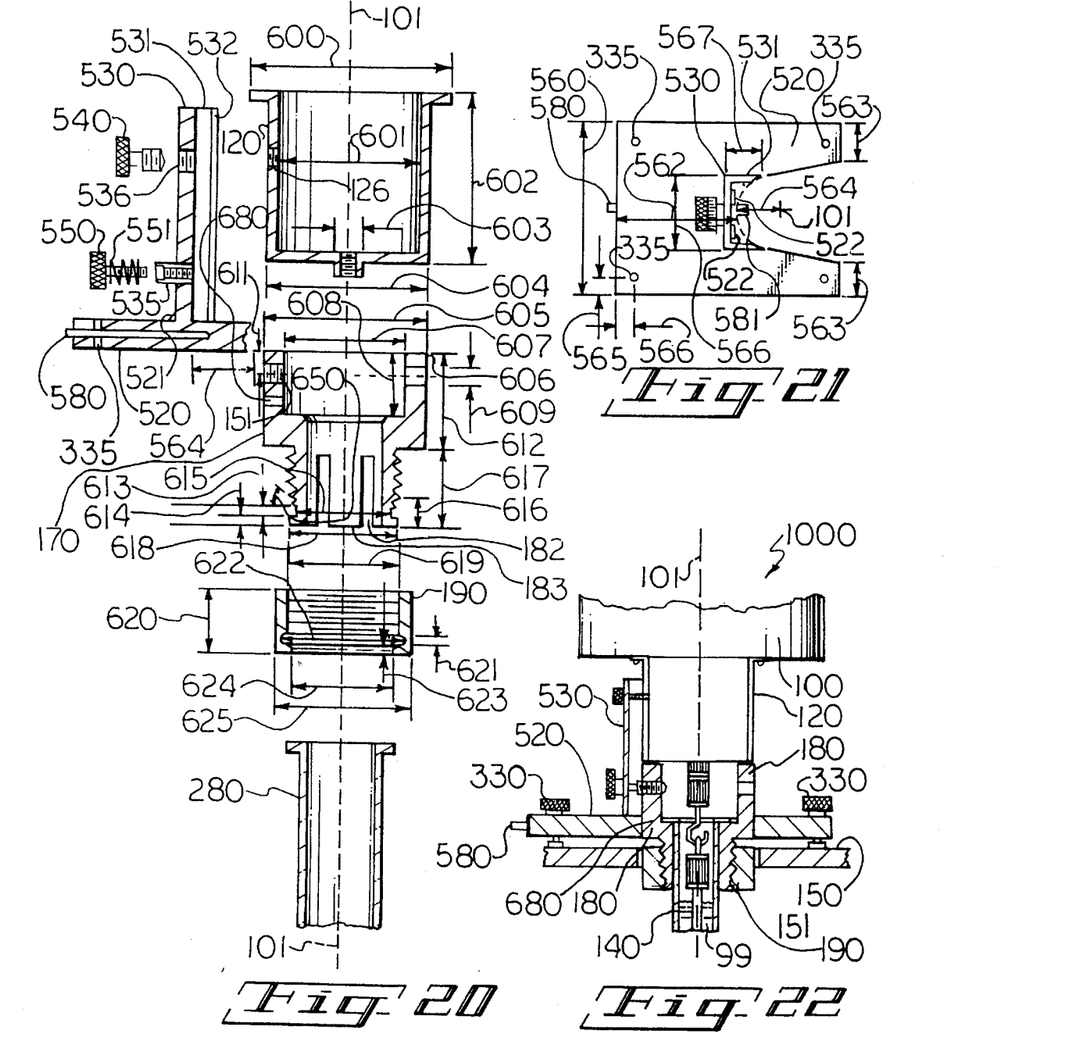
FIG. 20 is a side, cut-away, exploded view of the stator connector of FIG. 19.
FIG. 21 is a top view of part of a top portion of the stator connector of FIG. 19.
FIG. 22 is a side, cut-away view of the stator connector of FIG. 19, with stator, mounted on a sensitive rotating viscometer to improve the same.

In reference to FIGS. 19–22, the stator connector 300 preferably has parts of the stator collar and nut of the invention of Van Meter et al., Ser. No. 08/308,918, i.e., stator collar 170 and nut 190. These are attached to a base 520, which may be, for example, of three eighths of an inch aluminum, by means of screw 550, which screws into the collar 170, which is preferably made of DELRIN acetal homopolymer resin. The screw passes through upright support 530, which can be attached, for example, as in FIG. 20, by welds 521 if the base 520 and support 530 are both of metal, for example, aluminum. Preferably, as in FIG. 21, screws 522 secure support 530 into the base 520. Gluing, screwing, press fitting, riveting, and so forth are alternatives as well as is casting or molding the base and support in one piece. The upright support, base and collar assembly are attached to lower end 120 of the viscometer module 100, which lower end may be termed the rotor housing, as by screw 540 or other fastener. In practice, a screw 540, for example, a one quarter of an inch twenty-eight threads to the inch screw, passes through threaded hole 536 and into threaded hole 126 of the rotor housing 120 to fasten the base and support 520 & 530 to the rotor housing of a standard rotating viscometer such as the Model TAV-2 available from the Tannas Co., Midland, Mich., and the collar, nut and stator assembly is attached and removed thereafter in test set-up and take-down. Again, provision is made for leveling screws 330, which may have base 331. The rotor housing 120 may be attached to the viscometer module 100 with screws which pass through holes 124. The upright support 530 may have arms 531 which have bevels 532 to engage a part of the lower end 120 of the viscometer 100 and collar 170, to align and center these. Screw 550 may be accompanied by spring 551 for piloting into partially threaded barrel 535, for example, as in a stepped barrel with spring-ejected one quarter of an inch twenty-eight threads to the inch thumbscrew, which then engages corresponding threads 151 of the collar 170. Gas passage 580 may be present. Gas passage 680 may be present in the collar 170. Gas passage pin 581 helps locate collar 170 by use of passage 680 for easier attachment. Preferably, six slots 182 make six fingers 183 to provide for ease of applying inwardly directed pressure upon tightening of the nut 190. For example, the base 520 and support 530 may have the following dimensions:

| Feature | Dimension in Inches |
|---|---|
| Width 560 | 3.5 |
| Length 561 | 4.0 |
| Distance 562 | 1.5 |
| Width 563 | 0.5 |
| Radius 564 | 0.950 |
| Distance 565 | 0.25 |
| Width 566 | 1.5 |
| Length 567 | 0.5. |

Also, for example, the rotor housing 120, collar 170, and nut 190 may have the following dimensions:

| Feature | Dimension in Inches |
|---|---|
| Diameter 600 | 2.375 |
| Diameter 601 | 1.625 |
| Height 602 | 1.625 |
| Diameter 604 | 1.875 |
| Diameter 605 | 1.875 |
| Chamfer 606 | 0.625 |
| Diameter 607 | 1.375 |
| Hole Diameter 609 | 0.275 |
| Chamfer 610 | 0.625 |
| Height 611 | 0.375 |

-continued

| Feature | Dimension in Inches |
|---|---|
| Height 612 | 1.125 |
| Height 613 | 0.125 |
| Height 614 | 0.090 |
| Diameter 615 | 1.070 |
| Height 616 | 0.375 |
| Height 617 | 1.00 |
| Diameter 618 | 1.13 |
| Diameter 619 | 1.150 |
| Height 620 | 0.59 |
| U-Cut Height 621 | 0.125 |
| U-Cut Diameter 622 | 1.250 |
| Height 623 | 0.090 |
| Diameter 624 | 1.080 |
| Diameter 625 | 1.510. |

Threads 181, for example, may be provided at twelve per inch with a fifty-four thousandths of an inch thread surface and a one and one quarter inch outside diameter. Angle 650, for example, may be a sixty degree angle, and angle 651, for example, may be a thirty degree angle. Such dimensions and angles may be approximated.

In general, the stator connector components may be made of any suitable material or combination of materials such as engineering plastics, metals, glass, and so forth. They may be made by methods known in the art to include casting, molding, cutting, drilling, machining, milling, gluing, welding, pinning, riveting, screwing, and so forth and the like.

In general, the stator 280 may be of a standard length or of a length longer than standard stators for employment with sensitive rotating viscometers. They may be made of glass, plastic or metal, but preferably are of glass, and may be made by methods known in the art as those skilled therein appreciate.

CONCLUSION

The present invention is thus provided. Numerous modifications can be effected within its spirit, the literal claim scope of which is particularly pointed out as follows:

We claim:

1. In a sensitive rotating viscometer having a module in which resides a motor for rotating a rotor attachable to a shaft of the motor, the rotor having a longitudinal axis, and being rotatable about its longitudinal axis and being generally suspended from the shaft about a lower end of the viscometer module, the module connectable to a stator which is to contain a predetermined quantity of test fluid into which the rotor is immersed so that the rotor is concurrently suspended within the stator so that, when the rotor rotates therein, drag is created on the rotating rotor related to viscosity of the test fluid, the improvement which comprises a fixable stator connected to the module of the viscometer through a stator connector, wherein the stator connector attaches to the lower end of the viscometer module and comprises an attachment member which attaches to a side of the lower end of the viscometer module and holds the stator in place, without attaching to an opposing side of the lower end of the viscometer module.

2. The improvement of claim 1, which has means for leveling of the viscometer module.

3. The improvement of claim 1, wherein the attachment member is secured to the lower end of the viscometer module by means of a fastener, and the stator is secured in place by a stator collar which encircles and receives an upper end of the stator, which stator collar is secured to the attachment member, and which stator collar is positioned underneath the lower end of the viscometer module.

4. The improvement of claim 3, wherein a gas passage pin is present with the attachment member at a position facing the direction the stator collar is to be attached for securement to the attachment member and at a height which can help locate the stator collar having a gas passage present therein, which pin is insertable in the collar gas passage.

5. The improvement of claim 2, wherein the attachment member is secured to the lower end of the viscometer module by means of a fastener, and the stator is secured in place by a stator collar which encircles and receives an upper end of the stator, which stator collar is secured to the attachment member, and which stator collar is positioned underneath the lower end of the viscometer module.

6. The improvement of claim 5, wherein the fastener is a screw, and a gas passage pin is present with the attachment member at a position facing the direction the stator collar will be attached for securement to the attachment member and at a height which can help locate a stator collar which is the aforesaid stator collar but has a gas passage present therein, which pin is insertable in the collar gas passage.

7. A device useful in attachment of a stator to a viscometer module of a sensitive rotating viscometer, comprising a stator connector, which can attach to a lower end of the viscometer module of a sensitive rotating viscometer, and which includes a generally upright attachment member that can attach to a side of a lower end of the the viscometer module and can hold a stator in place, without attaching to an opposing side of the lower end of the viscometer module.

8. The device of claim 7, which can hold a stator collar which encircles and receives an upper end of the stator to hold the stator in place underneath the lower end of the viscometer module.

9. The device of claim 8, which further comprises the stator collar.

10. The device of claim 7, which has a means for leveling of the viscometer module wherein the means for leveling of the viscometer module includes a member in the form of a base extending laterally from the attachment member, and has leveling screws in holes in the member in the form of a base.

11. The device of claim 10, wherein the stator connector can hold a stator collar which encircles and receives an upper end of the stator to hold the stator in place underneath the lower end of the viscometer module.

12. The device of claim 11, wherein the stator connector has a screw hole for a screw to attach the attachment member to the side of the lower end of the viscometer module.

13. The device of claim 12, which further comprises the stator collar.

14. The device of claim 13, which has a gas passage pin present with the attachment member at a position facing the direction the stator collar will be attached for securement to the attachment member and at a height which can help locate a stator collar which is the aforesaid stator collar but which has a gas passage present therein, which pin is insertable in the collar gas passage.

15. The device of claim 12, which further has the screw to hold the stator collar.

16. The improvement of claim 3, wherein the fastener is a screw.

* * * * *